(12) United States Patent
Oganesian et al.

(10) Patent No.: US 9,570,634 B2
(45) Date of Patent: Feb. 14, 2017

(54) SENSOR PACKAGE WITH EXPOSED SENSOR ARRAY AND METHOD OF MAKING SAME

(71) Applicant: Optiz, Inc., Palo Alto, CA (US)

(72) Inventors: Vage Oganesian, Sunnyvale, CA (US); Zhenhua Lu, East Palo Alto, CA (US)

(73) Assignee: OPTIZ, INC., Palo Alto, CA (US)

( * ) Notice: Subject to any disclaimer, the term of this patent is extended or adjusted under 35 U.S.C. 154(b) by 0 days.

(21) Appl. No.: 14/824,966

(22) Filed: Aug. 12, 2015

(65) Prior Publication Data

US 2016/0043240 A1 Feb. 11, 2016

Related U.S. Application Data

(62) Division of application No. 14/292,744, filed on May 30, 2014, now Pat. No. 9,142,695.

(Continued)

(51) Int. Cl.
*H01L 31/0203* (2014.01)
*H01L 31/0232* (2014.01)
*H01L 27/146* (2006.01)
*G01N 27/414* (2006.01)
*H01L 23/053* (2006.01)

(52) U.S. Cl.
CPC ......... *H01L 31/0203* (2013.01); *G01N 27/414* (2013.01); *H01L 23/053* (2013.01); *H01L 27/14618* (2013.01); *H01L 27/14625* (2013.01); *H01L 27/14627* (2013.01); *H01L 31/02325* (2013.01); *H01L 2224/48091* (2013.01); *H01L 2224/73265* (2013.01); *H01L 2924/10156* (2013.01); *H01L 2924/16235* (2013.01); *H01L 2924/181* (2013.01); *H01L 2924/1815* (2013.01)

(58) Field of Classification Search
CPC ............... H01L 31/0203; H01L 23/053; H01L 27/14625; H01L 27/14618
See application file for complete search history.

(56) References Cited

U.S. PATENT DOCUMENTS 5,037,779 A   8/1991  Whalley et al.
6,627,864 B1  9/2003  Glenn
(Continued)

OTHER PUBLICATIONS

U.S. Appl. No. 13/157,193, filed Jun. 9, 2011, Oganesian, Vage.
(Continued)

*Primary Examiner* — Tucker J Wright
(74) *Attorney, Agent, or Firm* — DLA Piper LLP (US)

(57) ABSTRACT

A packaged sensor assembly and method of forming that includes a first substrate having opposing first and second surfaces and a plurality of conductive elements each extending between the first and second surfaces. A second substrate comprises opposing front and back surfaces, one or more detectors formed on or in the front surface, and a plurality of contact pads formed at the front surface which are electrically coupled to the one or more detectors. A third substrate is mounted to the front surface to define a cavity between the third substrate and the front surface, wherein the third substrate includes a first opening extending from the cavity through the third substrate. The back surface is mounted to the first surface. A plurality of wires each extend between and electrically connecting one of the contact pads and one of the conductive elements.

16 Claims, 18 Drawing Sheets

Related U.S. Application Data

(60) Provisional application No. 61/830,563, filed on Jun. 3, 2013, provisional application No. 61/831,397, filed on Jun. 5, 2013.

(56) References Cited

U.S. PATENT DOCUMENTS

| | | |
|---|---|---|
| 6,777,767 B2 | 8/2004 | Badehi |
| 6,972,480 B2 | 12/2005 | Zilber et al. |
| 7,033,664 B2 | 4/2006 | Zilber et al. |
| 7,157,742 B2 | 1/2007 | Badehi |
| 7,192,796 B2 | 3/2007 | Zilber et al. |
| 7,265,440 B2 | 9/2007 | Zilber et al. |
| 7,456,901 B2 | 11/2008 | Jeong et al. |
| 7,495,341 B2 | 2/2009 | Zilber et al. |
| 7,569,409 B2 | 8/2009 | Lin et al. |
| 7,576,401 B1 * | 8/2009 | de Guzman ........... G02B 7/021 257/234 |
| 7,589,422 B2 | 9/2009 | Lee et al. |
| 7,642,629 B2 | 1/2010 | Zilber et al. |
| 7,664,390 B2 | 2/2010 | Cho et al. |
| 7,859,033 B2 | 12/2010 | Brady |
| 8,432,011 B1 | 4/2013 | Oganesian |
| 2004/0080642 A1 | 4/2004 | Kobayashi et al. |
| 2004/0142539 A1 | 7/2004 | Koizumi |
| 2004/0251525 A1 | 12/2004 | Zilber |
| 2005/0051859 A1 | 3/2005 | Hoffman |
| 2005/0104179 A1 | 5/2005 | Zilber |
| 2005/0104186 A1 | 5/2005 | Yang |
| 2005/0139848 A1 | 6/2005 | Yee |
| 2005/0205977 A1 | 9/2005 | Zilber |
| 2007/0054419 A1 | 3/2007 | Paik et al. |
| 2007/0138498 A1 | 6/2007 | Zilber |
| 2007/0190691 A1 | 8/2007 | Humpston |
| 2007/0190747 A1 | 8/2007 | Humpston |
| 2008/0012115 A1 | 1/2008 | Zilber |
| 2008/0017879 A1 | 1/2008 | Zilber |
| 2008/0083976 A1 | 4/2008 | Haba |
| 2008/0083977 A1 | 4/2008 | Haba |
| 2008/0099900 A1 | 5/2008 | Oganesian |
| 2008/0099907 A1 | 5/2008 | Oganesian |
| 2008/0116544 A1 | 5/2008 | Grinman |
| 2008/0116545 A1 | 5/2008 | Grinman |
| 2008/0150065 A1 * | 6/2008 | Oda ................... H01L 31/0203 257/434 |
| 2008/0150121 A1 | 6/2008 | Oganesian |
| 2008/0164413 A1 | 7/2008 | Shibayama |
| 2008/0185671 A1 | 8/2008 | Huang et al. |
| 2008/0191343 A1 | 8/2008 | Liu |
| 2008/0246136 A1 | 10/2008 | Haba |
| 2008/0265350 A1 | 10/2008 | Wu et al. |
| 2009/0038843 A1 | 2/2009 | Yoneda et al. |
| 2009/0115047 A1 | 5/2009 | Haba |
| 2009/0160065 A1 | 6/2009 | Haba |
| 2009/0212381 A1 | 8/2009 | Crisp |
| 2009/0284631 A1 | 11/2009 | Matsuo et al. |
| 2009/0309177 A1 | 12/2009 | Jeung et al. |
| 2010/0002107 A1 | 1/2010 | Harazono |
| 2010/0032781 A1 | 2/2010 | Ryu |
| 2010/0053318 A1 | 3/2010 | Sasaki |
| 2010/0053407 A1 | 3/2010 | Crisp |
| 2010/0200898 A1 | 8/2010 | Lin et al. |
| 2010/0225006 A1 | 9/2010 | Haba |
| 2010/0230812 A1 | 9/2010 | Oganesian |
| 2010/0237452 A1 | 9/2010 | Hagiwara et al. |
| 2010/0244171 A1 | 9/2010 | Nagamatsu et al. |
| 2011/0012259 A1 | 1/2011 | Grinman |
| 2011/0024610 A1 | 2/2011 | Tu et al. |
| 2011/0031629 A1 | 2/2011 | Haba |
| 2011/0033979 A1 | 2/2011 | Haba |
| 2011/0049696 A1 | 3/2011 | Haba |
| 2011/0108940 A1 | 5/2011 | Huang et al. |
| 2011/0187007 A1 | 8/2011 | Haba |
| 2012/0018863 A1 | 1/2012 | Oganesian |
| 2012/0018868 A1 | 1/2012 | Oganesian |
| 2012/0018893 A1 | 1/2012 | Oganesian |
| 2012/0018894 A1 | 1/2012 | Oganesian |
| 2012/0018895 A1 | 1/2012 | Oganesian |
| 2012/0020026 A1 | 1/2012 | Oganesian |
| 2012/0043635 A1 | 2/2012 | Yang |
| 2012/0068327 A1 | 3/2012 | Oganesian |
| 2012/0068330 A1 | 3/2012 | Oganesian |
| 2012/0068351 A1 | 3/2012 | Oganesian |
| 2012/0068352 A1 | 3/2012 | Oganesian |
| 2012/0313207 A1 * | 12/2012 | Oganesian ............ H01L 24/19 257/433 |
| 2014/0015086 A1 | 1/2014 | Yu et al. |
| 2014/0035078 A1 | 2/2014 | Jan |
| 2014/0041214 A1 | 2/2014 | Barlow |

OTHER PUBLICATIONS

U.S. Appl. No. 13/157,202, filed Jun. 9, 2011, Oganesian, Vage.
U.S. Appl. No. 13/157,207, filed Jun. 9, 2011, Oganesian, Vage.
U.S. Appl. No. 13/186,357, filed Jul. 19, 2011, Oganesian, Vage.
U.S. Appl. No. 13/225,092, filed Sep. 2, 2011, Oganesian, Vage.
U.S. Appl. No. 13/301,683, filed Nov. 21, 2011, Oganesian, Vage.
U.S. Appl. No. 13/343,682, filed Jan. 4, 2012, Oganesian, Vage.
U.S. Appl. No. 13/427,604, filed Mar. 22, 2012, Oganesian, Vage.
U.S. Appl. No. 13/356,328, filed Jan. 23, 2012, Oganesian, Vage.
U.S. Appl. No. 13/468,632, filed May 10, 2012, Oganesian, Vage.
U.S. Appl. No. 13/559,510, filed Jul. 26, 2012, Oganesian, Vage.
U.S. Appl. No. 13/423,045, filed Mar. 16, 2012, Oganesian, Vage.
U.S. Appl. No. 13/609,002, filed Sep. 10, 2012, Oganesian, Vage.
U.S. Appl. No. 13/312,826, filed Dec. 2011, Organesian.

* cited by examiner

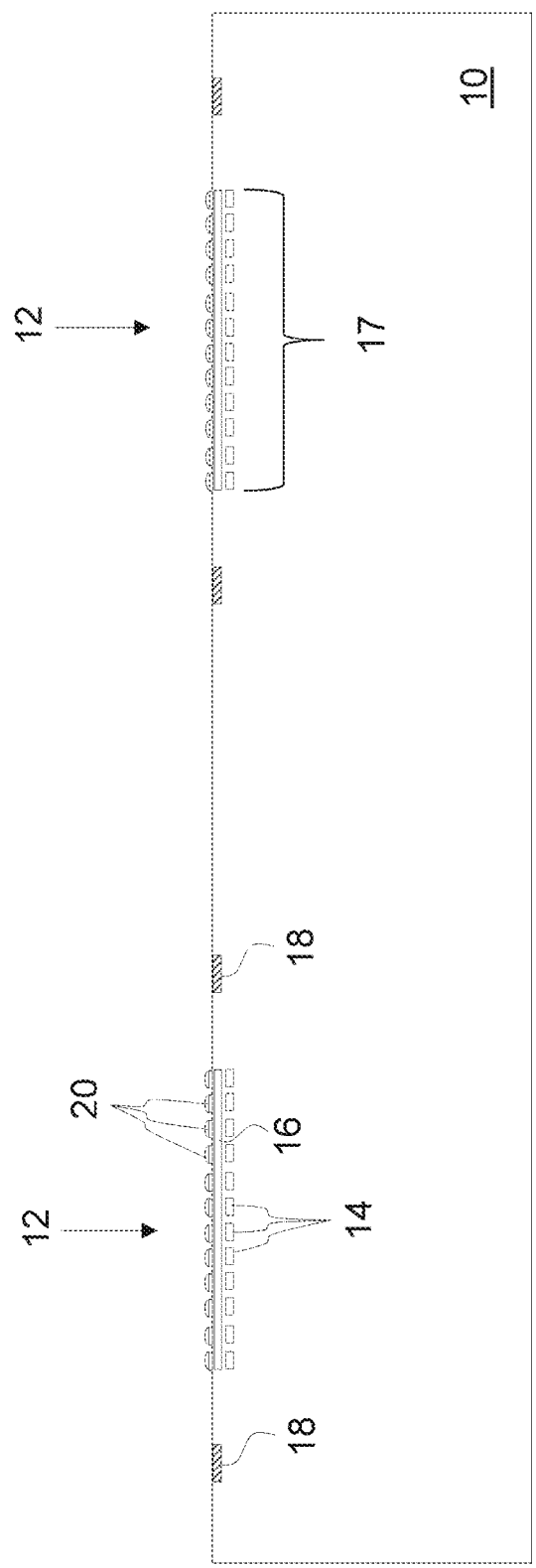
FIG. 1A
FIG. 1B

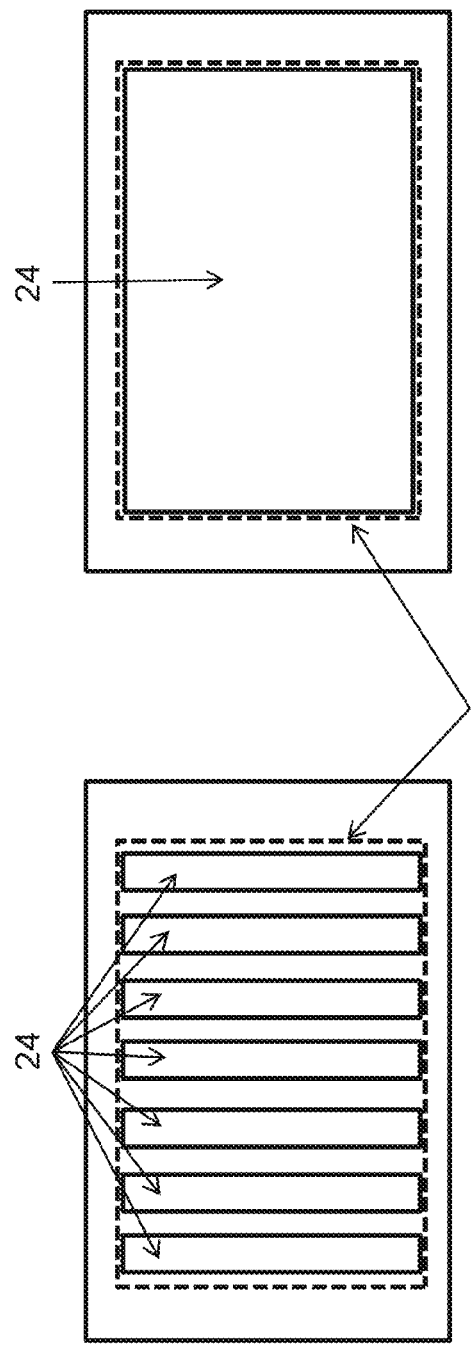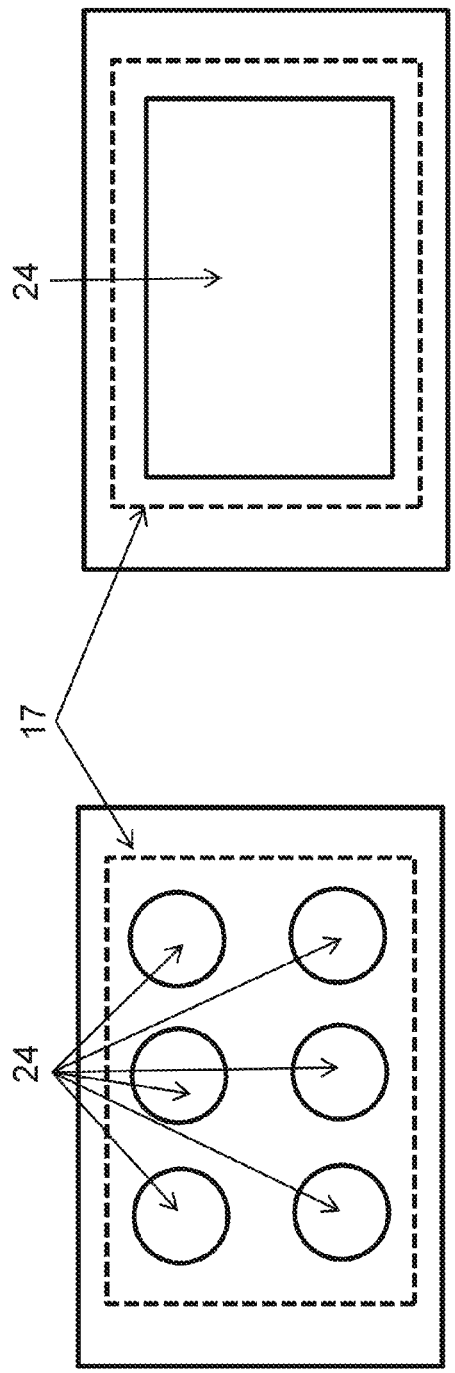

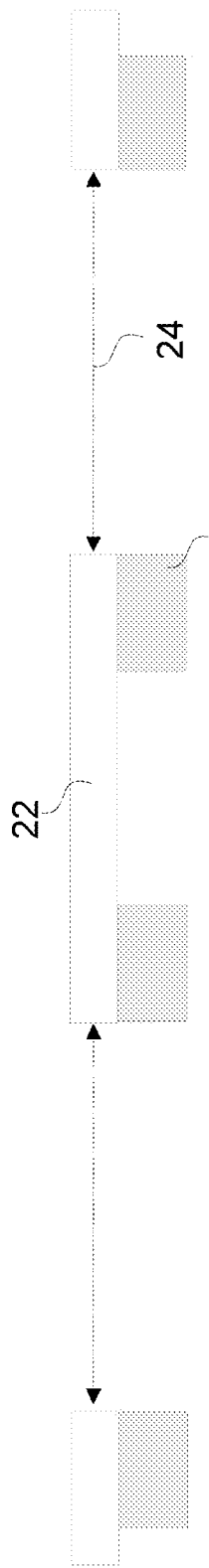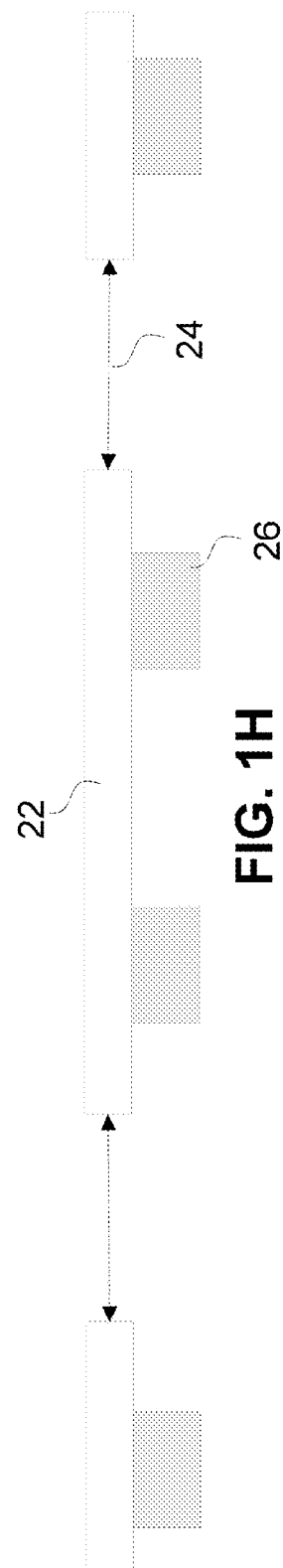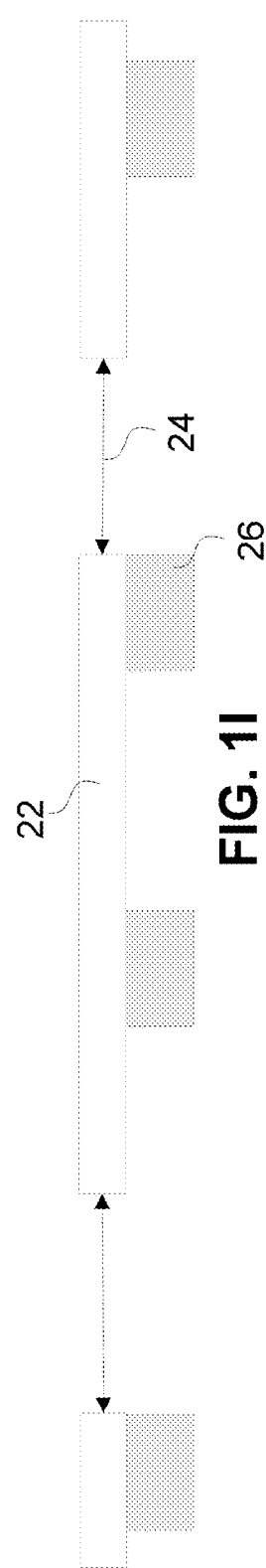

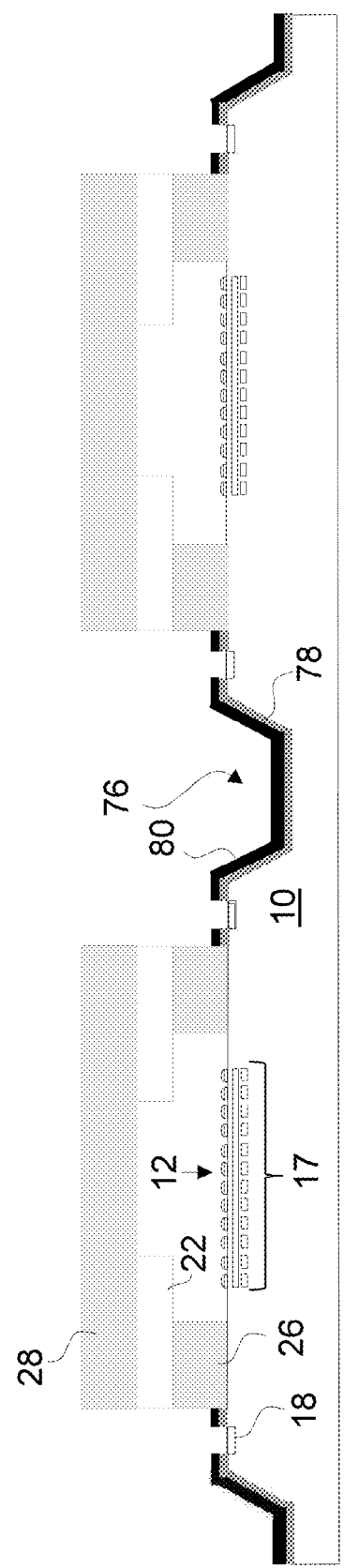

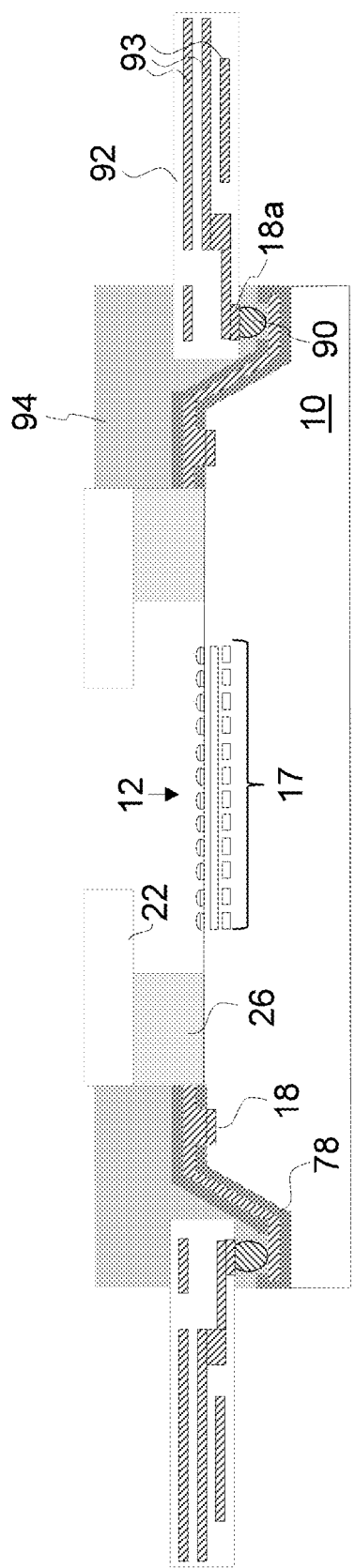

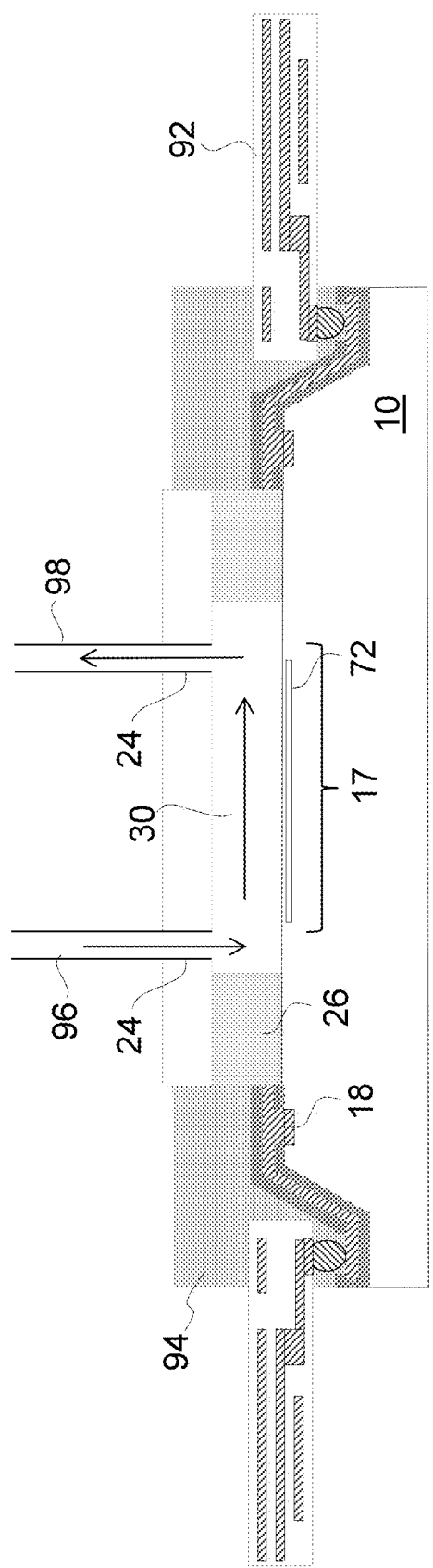

SENSOR PACKAGE WITH EXPOSED SENSOR ARRAY AND METHOD OF MAKING SAME

RELATED APPLICATIONS

This application is a divisional of U.S. application Ser. No. 14/292,744, filed May 30, 2014, which claims the benefit of U.S. Provisional Application Nos. 61/830,563, filed Jun. 3, 2013, and 61/831,397, filed Jun. 5, 2013, and which are incorporated herein by reference.

FIELD OF THE INVENTION

The present invention relates to packaging of microelectronic sensor devices such as image sensors and chemical sensors, and more particularly to a sensor package that leaves the sensor protected, electrically connected, yet exposed.

BACKGROUND OF THE INVENTION

The trend for semiconductor devices is smaller integrated circuit (IC) devices (also referred to as chips), packaged in smaller packages (which protect the chip while providing off chip signaling connectivity). One example are image sensors, which are IC devices that include photo-detectors which transform incident light into electrical signals.

Image sensors are typically encapsulated in a package that protects the sensor from contamination, and provides the off chip signaling connectivity. One issue, however, is that transparent substrates used to encapsulate the optical sensor can adversely affect the light passing therethrough and onto the sensor (e.g. distortion and photon loss). Another type of sensor is a chemical sensor that detects physical substances such as gases and chemicals. However, in order to operate, the chemical sensor cannot be sealed off from the environment, yet it is still desirable to package such sensors for protection and off chip signaling connectivity.

Conventional sensor packages are disclosed in U.S. Patent Publications 2005/0104186 and 2005/0051859, and in U.S. Pat. No. 6,627,864. Each of the disclosed sensor packages includes a sensor chip, a host substrate such as a silicon member, a PCB or a Flex-PCB, a window opening for the sensor area, and a transparent glass that hermetically seals the sensor area. Optionally and frequently, the sealed area is filled with transparent epoxy to improve bonding strength between the sensor die and the host substrate, which sacrifices at least some of the photon sensor's sensitivity. The transparent glass is to protect the sensor area from contaminants and moisture while also providing additional substrate strength and rigidity to the package. The sensor chip is usually mounted on to the host substrate by a flip-chip or wire bonding technique. This allows the sensor bond pads to connect with a plurality of metal traces on the surface of host substrate through an interconnect such as ball grid array (BGA). Metal traces are generally deposited on the surface of the host substrate, which typically consists of a single layer of circuitry. However, it is difficult to achieve reduced sizes with these configurations and prevent sensor area contamination during the assembly process.

There is a need for an improved package and packaging technique that provides the sensor with some protection with off chip signaling connectivity, yet leaves the sensor exposed to what is being detected. There is also a need for improved attachment and connectivity schemes with supporting host substrates.

BRIEF SUMMARY OF THE INVENTION

The aforementioned problems and needs are addressed by a packaged sensor assembly that includes a first substrate having opposing first and second surfaces and a plurality of conductive elements each extending between the first and second surfaces. A second substrate comprises opposing front and back surfaces, one or more detectors formed on or in the front surface, and a plurality of contact pads formed at the front surface which are electrically coupled to the one or more detectors. A third substrate is mounted to the front surface to define a cavity between the third substrate and the front surface, wherein the third substrate includes a first opening extending from the cavity through the third substrate. The back surface is mounted to the first surface. A plurality of wires each extend between and electrically connecting one of the contact pads and one of the conductive elements.

A method of forming a packaged sensor assembly includes providing a first substrate having opposing first and second surfaces, forming a plurality of conductive elements each extending between the first and second surfaces, providing a second substrate (that includes opposing front and back surfaces, one or more detectors formed on or in the front surface, and a plurality of contact pads formed at the front surface which are electrically coupled to the one or more detectors), mounting a third substrate to the front surface to define a cavity between the third substrate and the front surface, wherein the third substrate includes a first opening extending from the cavity through the third substrate, mounting the back surface to the first surface, and providing a plurality of wires each extending between and electrically connecting one of the contact pads and one of the conductive elements.

Other objects and features of the present invention will become apparent by a review of the specification, claims and appended figures.

BRIEF DESCRIPTION OF THE DRAWINGS

FIGS. 4A-4F are cross sectional side views showing in sequence the steps in forming an alternate embodiment of the packaged sensor assembly.

FIGS. 5A-5B are cross sectional side views showing multiple openings in the protective substrate for providing a flow of physical substances across the sensor.

DETAILED DESCRIPTION OF THE INVENTION

The present invention is a packaging solution that offers protection to the sensor chip, provides off chip signaling connectivity, is minimal in size, and can be reliability manufactured.

Figure 1J:
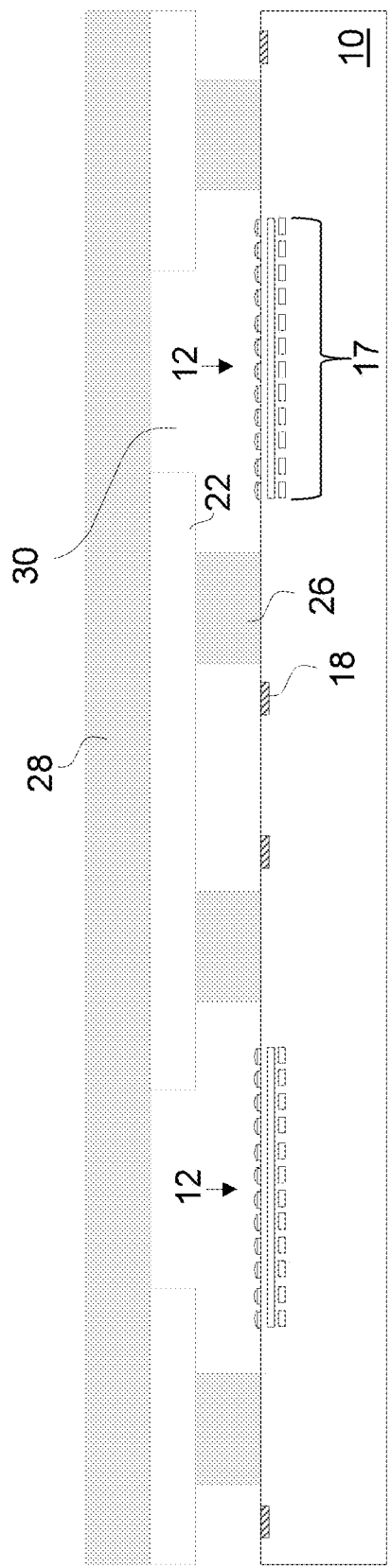
FIGS. 1A-1P are cross sectional side views showing in sequence the steps in forming the packaged sensor assembly for an image sensor.
Figure 1K:
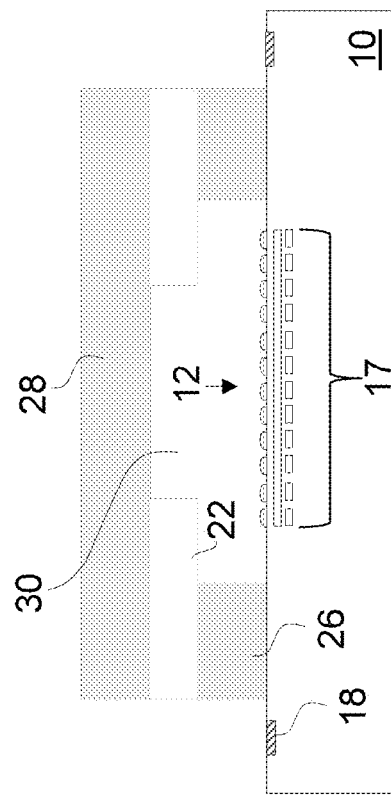
Figure 1L:
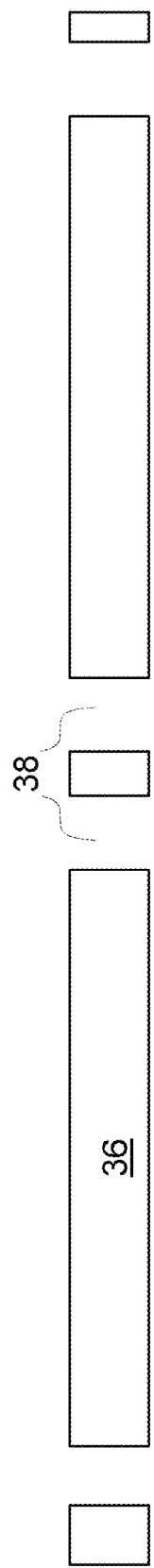
Figure 1M:
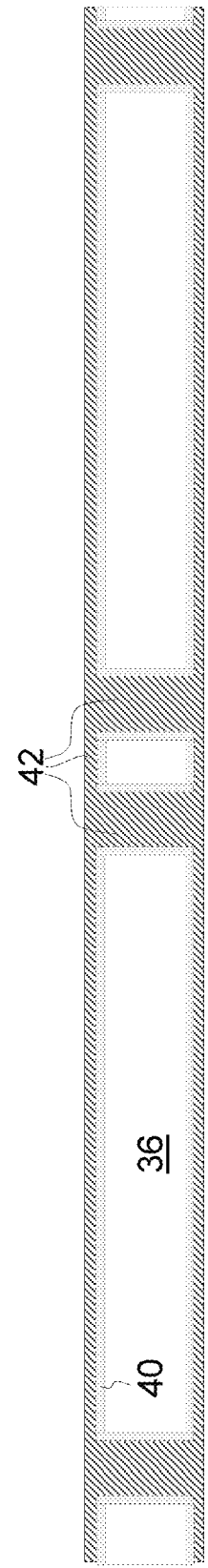
Figure 1N:
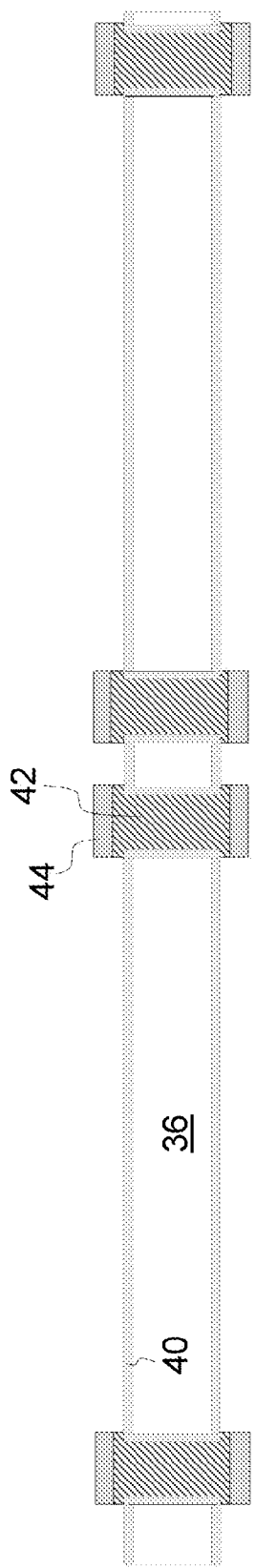
Figure 1O:
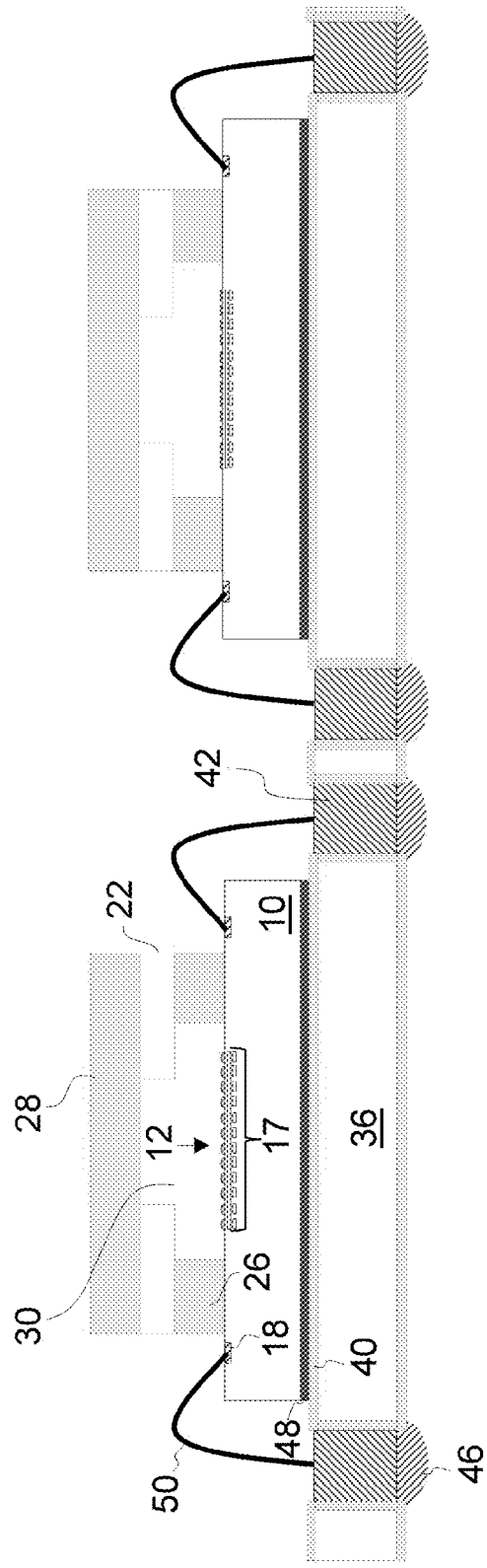
Figure 1P:
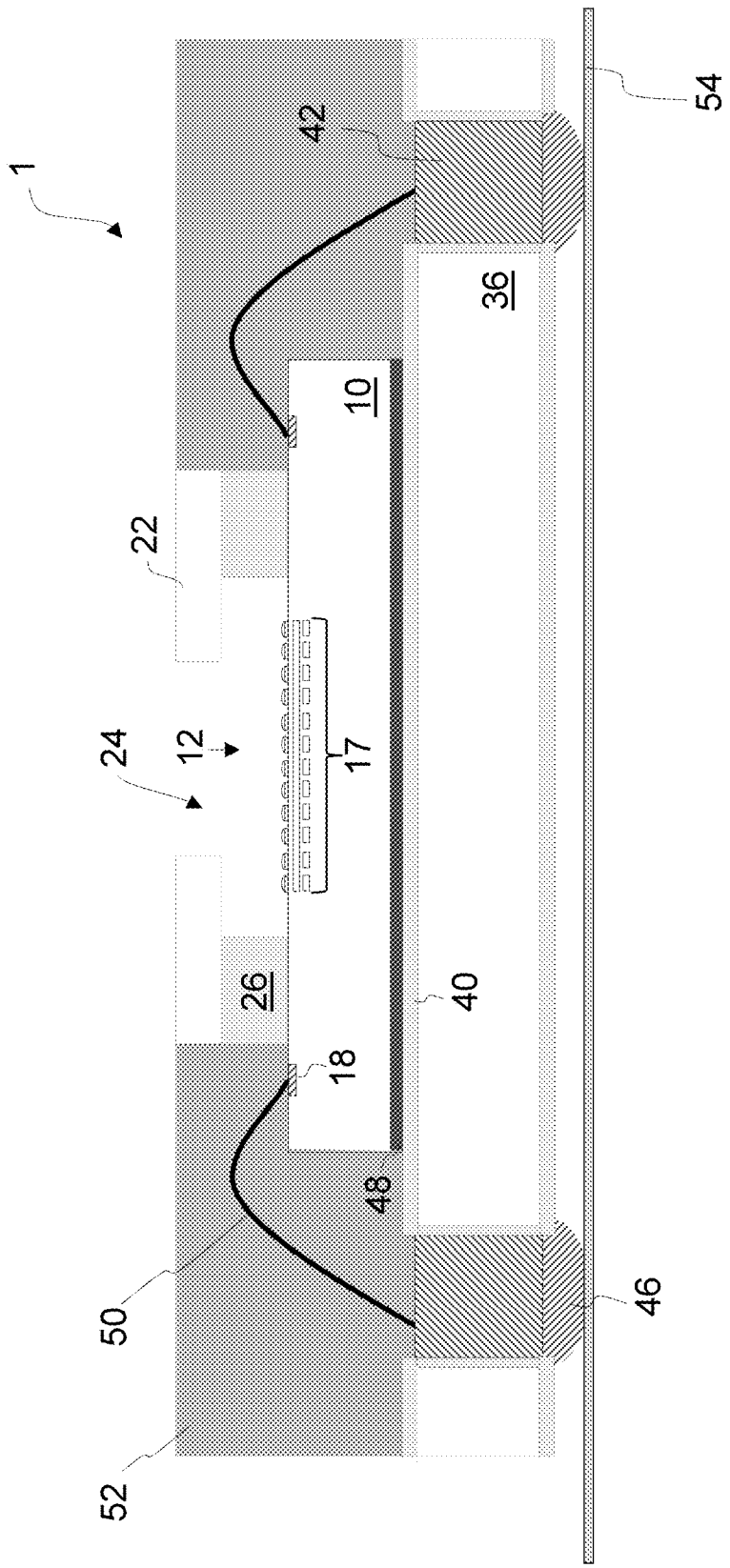

FIGS. 1A-1P illustrate the formation of the packaged sensor assembly 1. The formation begins with a wafer 10 (substrate) containing multiple sensors 12 formed thereon, as illustrated in FIG. 1A. For the purposes of illustration, the formation of the packaged sensor will be described with respect to an optical sensor, but any sensor can be used (e.g. chemical sensors, etc.). Each image sensor 12 includes a plurality of photo detectors 14, supporting circuitry 16, and contact pads 18. Sensors 12 are configured to detect and measure light incident on the active area 17 of each sensor 12. The contact pads 18 are electrically connected to the photo detectors 14 and/or their supporting circuitry 16 for providing off chip signaling. Each photo detector 14 converts light energy to a voltage signal. Additional circuitry may be included to amplify the voltage, and/or convert it to digital data. Color filters and/or microlenses 20 can be mounted over the photo detectors 14. Sensors of this type are well known in the art, and not further described herein.

A protective substrate with sensor window openings is formed next. The protective substrate 22 can be glass or any other optically transparent or semi-transparent rigid substrate. Glass is the preferred material. Glass thickness in range of 50 to 1500 μm is preferred. Sensor area window openings 24 are formed in protective substrate 22 by, for example, laser, sandblasting, etching or any other appropriate cavity forming methods. The openings 24 formed in the protective substrate 22 are illustrated in FIG. 1B. The sidewalls of the openings 24 can be vertical as shown, or can be tapered inwardly or outwardly. Preferably, the opening 24 are equal in size or smaller than the underlying active areas 17 over which they will be placed, as illustrated in FIGS. 1D and 1F respectively. Alternately, there can be multiple openings 24 for each active area 17, as illustrated in FIGS. 1C and 1E. Each active area will have at least one opening 24. Openings 24 can be any shape or size that is compatible for the particular sensor functionality. The openings 24 will benefit image sensors by eliminating distortion and photon loss caused by the optically transparent protective substrates found in a traditional image sensor packages. The opening 24 can also expose the sensor active areas 17 to the environment, allowing chemical sensor detectors to detect physical substances such as gas and chemicals to which the sensor is exposed.

An optional layer of spacer material 26 is deposited on the protective substrate 22, either before or after openings 24 are formed. The spacer material 26 can be polymer, epoxy and/or any other appropriate material(s). Deposition can be implemented by roller, spray coating, screen printing or any other appropriate method(s). The thickness of the deposited material can be in the range of 5 to 500 μm. The spacer material 26 can be aligned to the edges of openings 24 as shown in FIG. 1G, spaced away from the edges of openings 24 as shown in FIG. 1H, or a combination of both as shown in FIG. 1I. Preferably, spacer material 26 is located to avoid contact with the active areas 17 and the contact pads 18 of the substrate 10 on which it is mounted (e.g. can be located between the active areas 17 and their respective contact pads 18).

The protective structure (substrate 22 and spacer material 26) is bonded to the active side of substrate 10 using a bonding agent. The bonding agent can be epoxy deposited by roller and then heat cured or any other appropriate bonding methods that are well-known in the art. A protective tape 28 is placed over the protective substrate 22, forming a hermetic sealed cavity 30 for each image sensor 12. The height of cavities 30 is preferably in the range of 5 to 500 μm. Cavities 30 can be filled with gas, liquid, or be expelled of all gas by creating a vacuum. The substrate 10 can optionally be thinned by removing material from its back side. In the case of a silicon substrate 10, silicon thinning can be done by mechanical grinding, chemical mechanical polishing (CMP), wet etching, atmospheric downstream plasma (ADP), dry chemical etching (DCE), or a combination of aforementioned processes or any another appropriate silicon thinning method(s). The thickness of thinned substrate 10 is in range of 100 to 2000 μm. The resulting structure is shown in FIG. 1J.

Portions of the protective substrate 22 between sensors 12 and over contact pads 18 can be removed using laser cutting equipment, mechanical sawing, a combination of aforementioned processes or any other appropriate glass cutting method(s). Laser cutting is the preferred method of cutting. This process separates each protective cavity 30 from other protective cavities for other sensors 12, thus achieving protective cavity singulation. This step also exposes the sensor pads 18. Substrate 10 is then singulated/diced to separate each sensor 12 and its respective packaging. Wafer level dicing/singulation can be done with mechanical blade dicing equipment, laser cutting or any other appropriate processes. The resulting structure is shown in FIG. 1K.

A host substrate assembly 34 is formed by first providing a host substrate 36, which can be organic Flex PCB, FR4 PCB, silicon (rigid), glass, ceramic or any other type of packaging substrate. VIA (Vertical Interconnect Access) openings 38 can be made through the host substrate 36 by mechanical drilling, laser, dry etch, wet etch or any another appropriate VIA opening forming method(s) that are well known in the art. Preferably, a laser is used to form the VIA openings 38. The VIA opening walls can be tapered to form a funnel shape or both the top and bottom portions of the VIA are of the same dimension to form a cylinder shape. The resulting structure is shown in FIG. 1L.

A layer of dielectric material 40 is formed over all surfaces of host substrate 36 (including the sidewalls of the VIA openings 38). Layer 40 is desirable if the host substrate 36 is made of a conductive material such as conductive silicon. The dielectric material layer 40 can be silicon dioxide deposited by Physical Vapor Deposition (PVD). If the host substrate 36 is made of non-conductive organic material such as flex PCB or FR4 Resin, then dielectric layer 40 can be omitted. Electrically conductive material 42 is then formed over all surfaces of the host substrate 36 (including partially or completely filing VIA openings 38). Electrically conductive material 42 can be copper, aluminum, conductive polymer or any other appropriate electric conductive material(s). The electrically conductive material 42 can be deposited by Physical Vapor Deposition (PVD), Chemical Vapor Deposition (CVD), plating or any other appropriate deposition method(s). The sidewalls of VIA openings 38 can be coated with the conductive material 42, or the VIA openings 38 can be entirely filled with the conductive material 42 as shown in FIG. 1M.

A layer of photoresist 44 is deposited over both top and bottom surfaces of the host substrate 36. The photoresist deposition method can be spray coating or any another appropriate deposition method(s). The photoresist 44 is exposed and etched using appropriate photolithography processes that are well known in the art, leaving the photoresist 44 only over the VIA openings 38 and pathways that will eventually form traces. A conductive material etch is performed to remove exposed portions of the conductive layer 42 (i.e. those portions not underneath the remaining photoresist 44). For example, leads, contacts, rerouted contacts and traces can be formed by this etch, which could use dry or wet etching methods that are well-known in the art. The resulting structure is shown in FIG. 1N.

The photoresist is stripped using sulfuric acid, acetone or any other photoresist stripping method that are appropriate. An optional plating process (e.g Ni/Pd/Au) on the conductive material 42 can be performed. Interconnects 46 are formed on the conductive material 42 over the VIA openings 38 on the bottom side of the host substrate 36. Interconnects can be ball grid array (BGA), land grid array (LGA), bumping, copper pillar or any other appropriate interconnect methods. Ball grid array is one of the preferred methods of interconnection and it can be deposited by screen printing followed by a reflow process. The singulated substrates 10 (with sensors 12) described above are then attached to the host substrate using an appropriate adhesive 48 by, for example, depositing adhesive on the substrate 10, or the host substrate 36, or both, and picking/placing substrate 10 onto host substrate 36 followed by an appropriate curing process. Electrical interconnects between contact pads 18 and conductive material 42 in VIA openings 38 are added, which are preferably bonding wires 50 that are well known in the art. The resulting structure is shown in FIG. 1O.

An overmold material 52 is dispensed on the host substrate 36 and in-between the mounted sensors 12. The overmold material 52 can be epoxy, resins or any other overmold material(s) that are well-known in the art. The upper surface of the cured overmold material 52 is preferably lower than the upper surface of the protective substrate 22 and higher than the upper surface of the wire bond contacts. The host substrate 36 is then singulated along scribe lines between the mounted sensors 12. Dicing/singulation of packages can be done with mechanical blade dicing equipment, laser cutting or any other appropriate processes. The finished sensor package is mounted to a second host substrate 54 via interconnects 46. The second host substrate 54 can be Flex PCB, Rigid PCB or any other applicable substrates with contact pads and electrical interconnects. The protective tape 28 is then removed, thus exposing the active area 17 of the sensor 12 to the environment. The final packaged sensor assembly 1 is shown in FIG. 1P.

In the final structure, sensor 12 is protected by protective substrate that at most extends only partially over substrate 10, so that sensor 12 is exposed to the environment. Specifically, light incident on the structure can pass directly to sensor 12 without passing through any transparent protective substrates. Conductive material 42 in VIA openings 38 form pass through electrical contacts or conductive elements that extend through substrate 36, and between wires 50 and interconnects 46. Overmolding material 52 protects the wire 50 connections.

Figure 2:
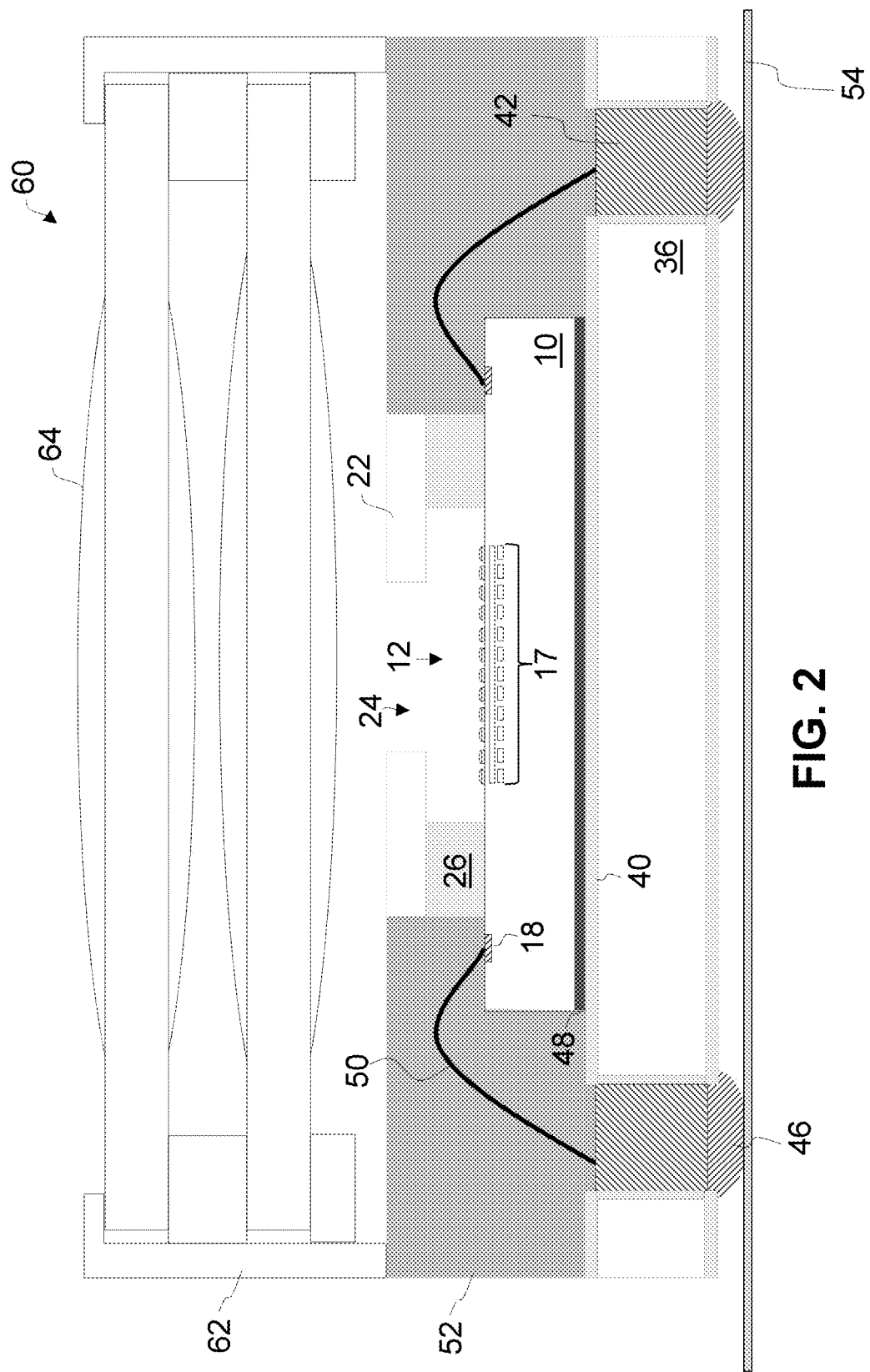
FIG. 2 is a cross sectional side view showing a lens module mounted to the packaged sensor assembly.

FIG. 2 illustrates a lens module 60 that can be mounted to the structure of FIG. 1P. Lens module 60 includes a housing 62 in which one or more lenses 64 are mounted to focus incoming light onto the image sensor 12 without having to pass through any protective substrates.

Figure 3:
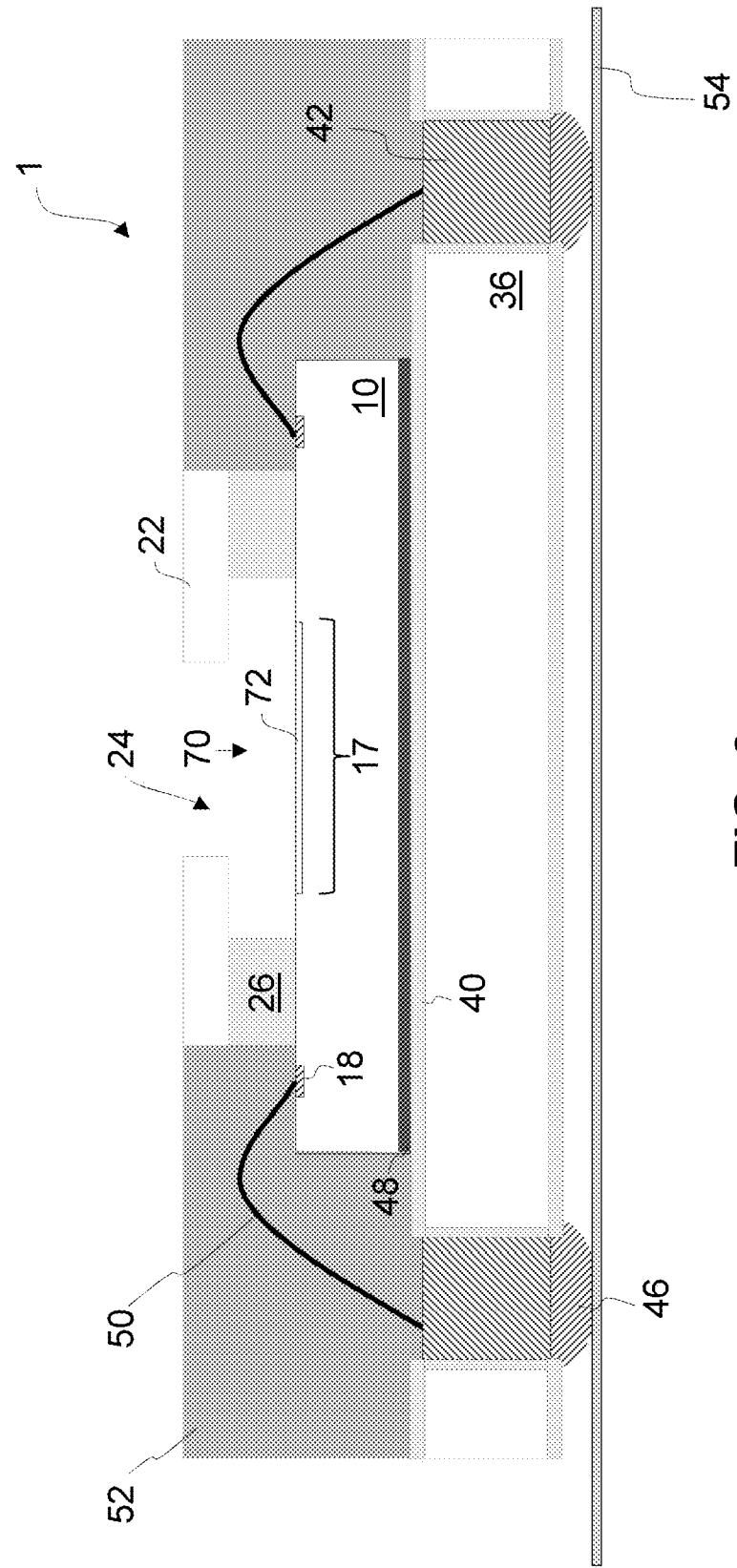
FIG. 3 is a cross sectional side view of an alternate embodiment showing the packaged sensor assembly for a chemical sensor.

FIG. 3 illustrates the packaged sensor assembly 1 with a chemical sensor 70 instead of an image sensor 12. Chemical sensor 70 includes one or more chemical detectors 72 formed on or in substrate 10 for detecting the presence of certain chemicals or particles that enter into cavity 30 through opening 24. Chemical detector 72 generates signals in response to the detected chemicals or particles, and provides those signals to contact pads 18. Chemical sensors of this type are well known in the art, and not further described herein.

Figure 4A:
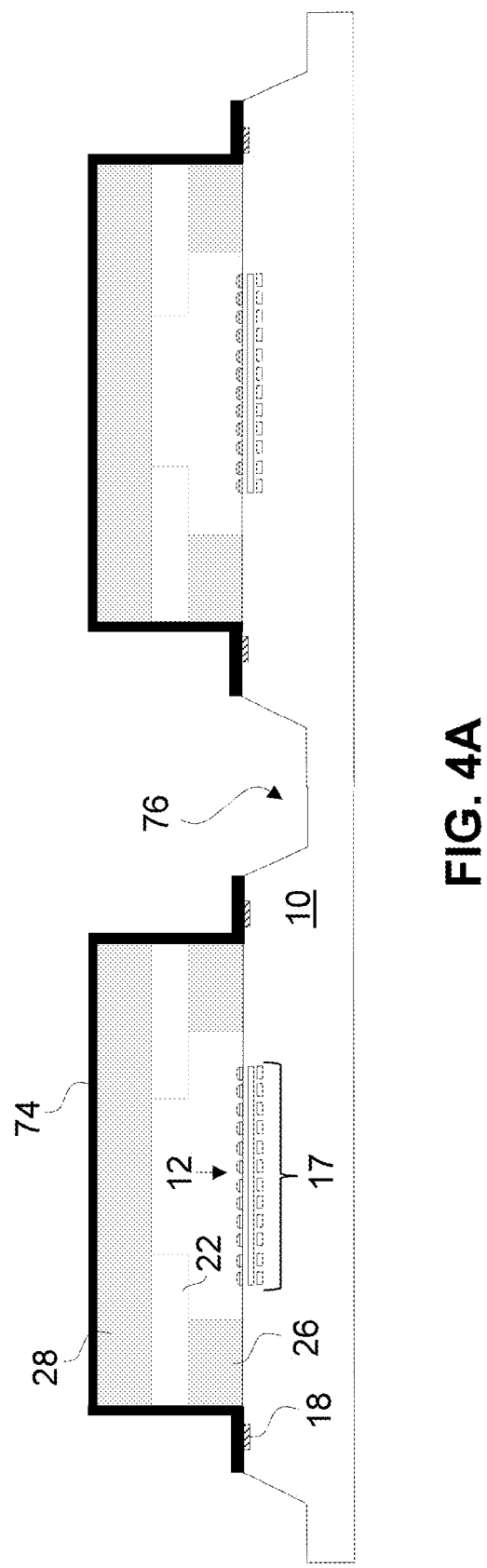

FIGS. 4A-4F illustrate the formation of an alternate embodiment of the packaged sensor assembly. The formation begins with the structure shown in FIG. 1K, but before dicing/singulation. A layer of photoresist 44 is deposited over the structure. Photoresist deposition can be achieved by spray coating or any another appropriate deposition method(s). The photoresist 74 is exposed and selectively etched using appropriate photolithography processes that are well known in the art. The cured/hardened photoresist 74 leaves portions of the substrate between sensors 12 exposed. The exposed portions of the substrate 10 are etched (e.g. by anisotropic dry etch) to form trenches into the top surface of substrate 10. An enchant of CF4, SF6, NF3, Cl2, CCl2F2 or any other appropriate etchant can be used. A preferred depth of the trenches 76 is in range of 5% to 50% of the substrate 10 thickness. The resulting structure is shown in FIG. 4A.

The photoresist 74 is stripped using acetone or any other dry plasma or wet photoresist stripping method that are well known in the art. A passivation layer of insulation material 78 such as silicon dioxide or silicon nitride is deposited over the structure. Preferably, passivation layer 78 is made of silicon dioxide and is at least 0.5 μm. Silicon dioxide deposition can be performed using Physical Vapor Deposition (PVD), PECVD or any another appropriate deposition method(s). A layer of photoresist 80 is deposited over the passivation layer 78. Photoresist 80 is exposed and selectively etched using appropriate photolithography processes that are well known in the art to remove those portions of the photoresist over the contact pads 18, and along and over the spacer material 26, the protective substrate 22 and the tape 28 (thus exposing the portions of the passivation layer 78 over these areas). The exposed portions of the passivation layer 78 are removed by, for example, plasma etching, to expose the contact pads 18, spacer material 26, protective substrate 22 and tape 28. If the passivation layer 78 is silicon dioxide, then an etchant of CF4, SF6, NF3 or any other appropriate etchant can be used. If the passivation layer 78 is silicon nitride, then an etchant of CF4, SF6, NF3, CHF3 or any other appropriate etchant can be used. The resulting structure is shown in FIG. 4B.

Figure 4C:
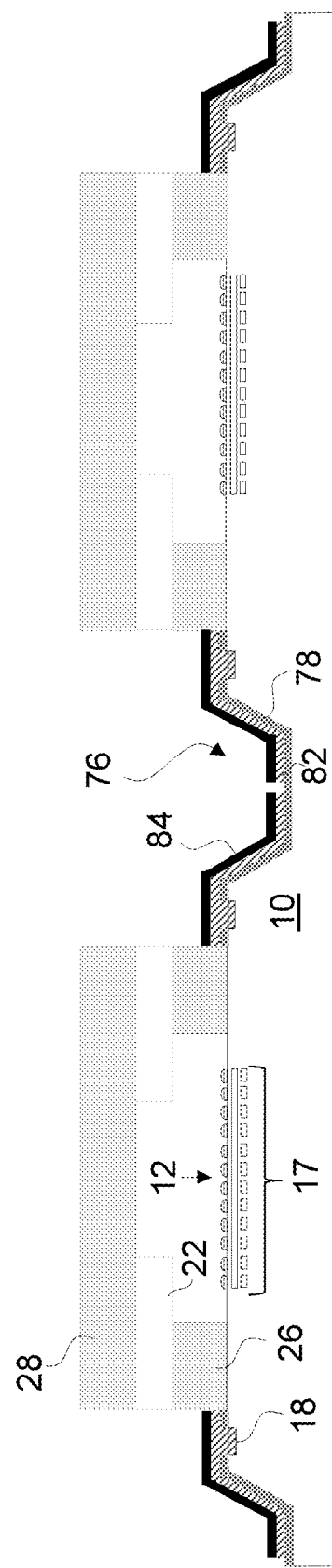

After the photoresist 80 is removed, an electrically conductive material 82 is deposited over the structure. The electrically conductive material 82 can be copper, aluminum, conductive polymer or any other appropriate electric conductive material(s). The electrically conductive material can be deposited by Physical Vapor Deposition (PVD), Chemical Vapor Deposition (CVD), plating or any other appropriate deposition method(s). Preferably, the electrically conductive material 82 is aluminum and is deposited by PVD. A layer of photoresist 84 is deposited over the structure. The photoresist 84 is exposed and etched using appropriate photolithography processes to form a mask over the electrically conductive layer 82 in the trenches 76 and over contact pads 18. The photo resist 84 is removed over the tape 28, the protective layer 22, spacer material 26 and optionally where the substrate 10 will be diced in the trenches 76, selectively exposing the electrically conductive layer 82 at those areas. The exposed portions of the electrically conductive layer 82 are removed, for example using dry or wet etching methods. The remaining portions of the electrically conductive layer 82 form a plurality of discrete traces (leads) each extending from one of the contact pads 18 down to the bottom of one of the trenches 76. Etchant for wet etch can be phosphoric acid (H3PO4), acetic acid, nitric acid (HNO3) or any other appropriate etchant(s). Etchant for dry etch can be Cl2, CCl4, SiCl4, BCl3 or any other appropriate etchant(s). Dry etch is a preferred method for this lead formation. Optionally, the electrically conductive material 82 can remain on the sidewall of protective substrate. The resulting structure is shown in FIG. 4C.

Figure 4D:
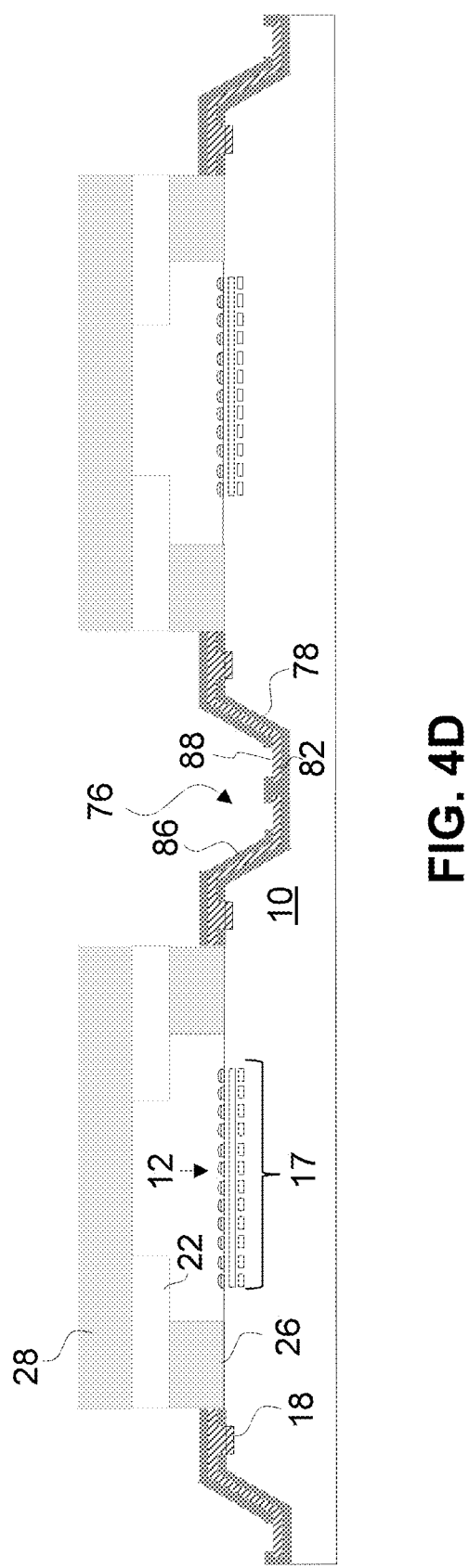

The remaining photoresist 84 is then removed. Optionally, a plating process (e.g. Ni/Pd/Au) can be performed on the leads (conductive layer 82). An optional encapsulant layer 86 is deposited over the conductive leads structure. The encapsulant layer 86 can be polyimide, ceramic, polymer, polymer composite, parylene, metallic oxide, silicon dioxide, silicon nitride, epoxy, silicone, porcelain, nitrides, glass, ionic crystals, resin, and a combination of aforementioned materials or any other appropriate dielectric material(s). The encapsulant layer 86 is preferably 0.1 to 2 μm in thickness, and the preferred material is liquid photolithography polymer such as solder mask which can be deposited by spray coating. A photolithography process is performed, where the developed/cured encapsulation 84 is removed except for over the leads. Rerouted contacts 88 can be created by forming openings in the encapsulation layer 86 at the bottom of the trenches 76. Optionally, the encapsulating material can remain on the sidewall of the protective substrate 22 and/or on the tape 28. The resulting structure is shown in FIG. 4D.

Wafer level dicing/singulation of components can be done with mechanical blade dicing equipment, laser cutting or any other appropriate processes, preferably at the bottom of trenches 76. An interconnect 90 can be formed on the rerouted contact pads or on the Flex-PCB. The interconnect 90 can be BGA, LGA, stud bump, plated bump, adhesive bump, polymer bump, copper pillar, micro-post or any other appropriate interconnecting method(s). Preferably, the interconnect 90 is made of an adhesive bump which is a composite of conductive material(s) and adhesive material(s). The conductive material(s) can be solder, silver, copper, aluminum, gold, a combination of aforementioned materials or any other appropriate conductive material(s). The adhesive material(s) can be varnish, resin, and a combination of aforementioned materials or any other appropriate adhesive material(s). The conductive adhesive can be deposited by pneumatic dispensing gun or any other appropriate dispensing method(s) and then cured by heat, UV or any other appropriate curing method(s) thus forming the bumps.

Figure 4F:
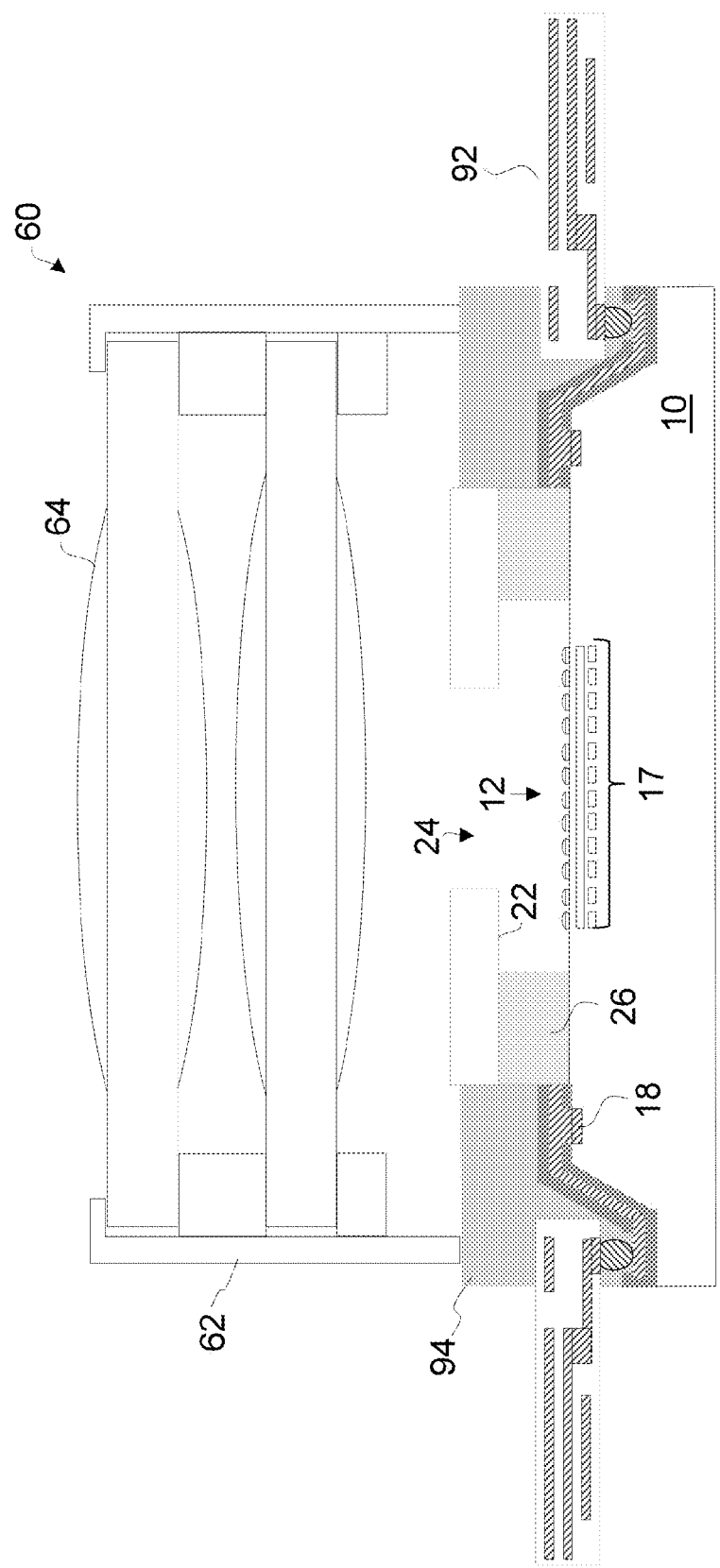

A flex-PCB can be mounted on all sides, three sides, two sides, or single side of the substrate 10. For example, two flex-PCBs 92 can be bonded to opposite sides of the substrate 10. Alternately, a single flex-PCB 92 with a window opening can be used, and extend off of one, two, three or all sides of substrate 10. The flex-PCB 92 can be any rigid or flexible substrate having one or more circuit layers 93 and contact pads 18a connected thereto. The interconnects 90 are electrically connected between the contact pads 18a and the conductive traces 82. The sensor package is placed inside of a pre-casted mold, and then an overmold compound 94 of choice is injected into the mold. Overmold material 94 can be epoxy, polymer, resins or any other overmold material(s) that are well-known in the art. The top surface of the cured overmold material can as high as the top surface of the protective substrate 22 but preferably does not extend any higher. The cured overmold material 94 preferably does not extend beyond substrate 10. Protective tape 28 is then removed, thus exposing the sensor active area to the environment. The resulting structure is shown in FIG. 4E. An optional lens module 60 as described above can be attached on the top of the structure, as shown in FIG. 4F.

The above described structure provides a Chip-On-Film (COF) package which is more compact than known packages. The thinner structure can be obtained by creating a step structure on the edge of the substrate die 10, then a plurality of metal traces and rerouted contact pads are formed on the second step surface, which connects to the top surface contact pads 18 via metal traces. A flexible cable and/or PCB is bonded to that second step surface. This structure lowers the altitude of the protective substrate 22 by bonding it directly onto the sensor die 10, rather than mounting it on a host substrate, thus reducing package thickness.

The above described structure also increases the image sensor's sensitivity through package structure. Specifically, greater photon sensitivity can be obtained by simply not obstructing the light path. By creating an opening 24 in the protective substrate 22 and not using any transparent underfill at the sensor area cavity, more photons are able to reach the active area with greater accuracy. Conventional devices rely on the protective substrate and transparent underfill to protect the sensor area by hermetically sealing it. However, the same hermetical seal can be achieved with the lens module 60. Lastly, better structural integrity is achieved by using overmold material 52/94 to enclose the entire bonding area rather than just applying a mold around the bonding surface as adhesive/underfill.

Figure 5A:
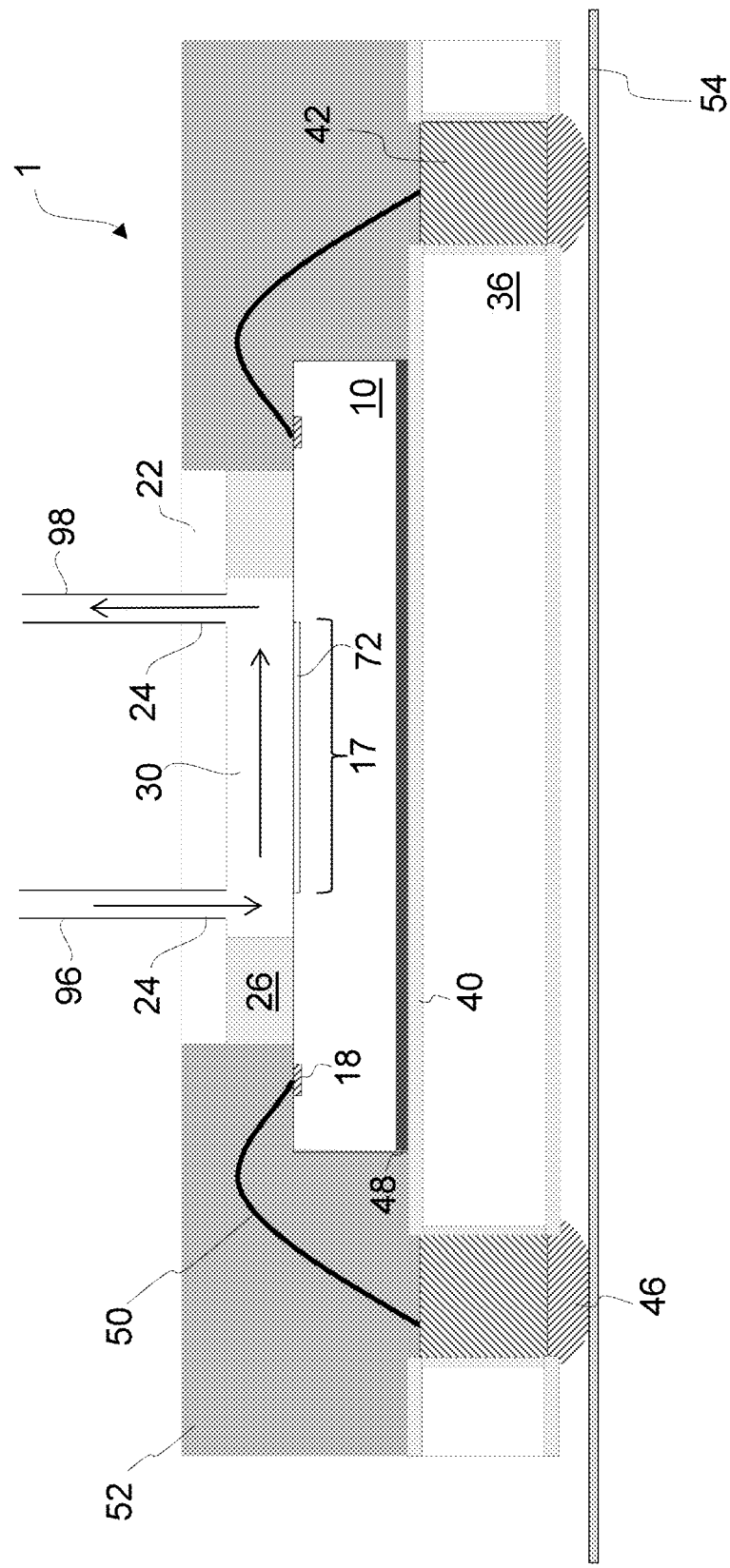
Figure 6:
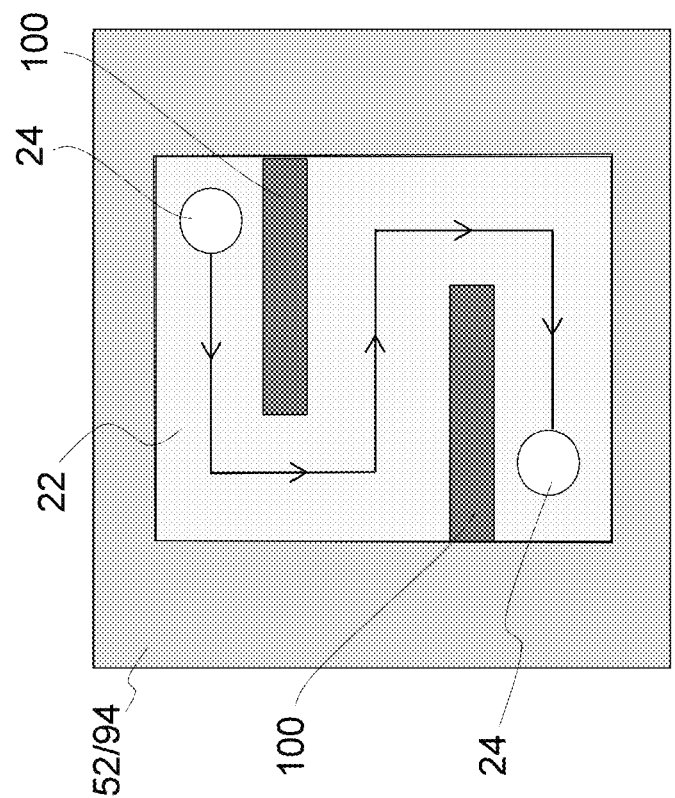
FIG. 6 is cross sectional side view showing multiple openings in the protective substrate and dam structures in the cavity for providing a non-linear flow of physical substances across the sensor.

For the chemical sensor embodiments, multiple openings 24 can be used to facilitate the flow of physical substances through the cavity 30 and over the sensor's active area. Input and output attachments 96 and 98 are connected to the openings 24 on the protective substrate 22, whereby physical substances such as gas or liquid flow through the packaged structure as indicated by the arrows in FIGS. 5A and 5B. Optional dam structures 100 can be included in cavity 30 to guide the physical substances through the cavity in a non-linear path, as shown in FIG. 6.

It is to be understood that the present invention is not limited to the embodiment(s) described above and illustrated herein, but encompasses any and all variations falling within the scope of the appended claims. For example, references to the present invention herein are not intended to limit the scope of any claim or claim term, but instead merely make reference to one or more features that may be covered by one or more of the claims. Materials, processes and numerical examples described above are exemplary only, and should not be deemed to limit the claims. Further, as is apparent from the claims and specification, not all method steps need be performed in the exact order illustrated or claimed, but rather in any order that allows the proper formation of the packaged sensor assembly 1. Lastly, single layers of material could be formed as multiple layers of such or similar materials, and vice versa.

It should be noted that, as used herein, the terms "over" and "on" both inclusively include "directly on" (no intermediate materials, elements or space disposed therebetween) and "indirectly on" (intermediate materials, elements or space disposed therebetween). Likewise, the term "mounted to" includes "directly mounted to" (no intermediate materials, elements or space disposed there between) and "indirectly mounted to" (intermediate materials, elements or spaced disposed there between), and "electrically coupled" includes "directly electrically coupled to" (no intermediate materials or elements there between that electrically connect the elements together) and "indirectly electrically coupled to" (intermediate materials or elements there between that electrically connect the elements together). For example, forming an element "over a substrate" can include forming the element directly on the substrate with no intermediate materials/elements therebetween, as well as forming the element indirectly on the substrate with one or more intermediate materials/elements therebetween.

What is claimed is:

1. A packaged sensor assembly, comprising:
a first substrate having opposing first and second surfaces and a plurality of conductive elements each extending between the first and second surfaces;
a second substrate that comprises:
opposing front and back surfaces,
one or more detectors formed on or in the front surface,
a plurality of contact pads formed at the front surface which are electrically coupled to the one or more detectors,
a third substrate mounted to the front surface, by spacer material directly disposed on the third substrate and an epoxy bonding agent disposed between the spacer material and the front surface, to define a cavity between the third substrate and the front surface, wherein the third substrate includes a first opening extending from the cavity through the third substrate, wherein the back surface is mounted to the first surface;
a plurality of wires each extending between and electrically connecting one of the contact pads and one of the conductive elements;
overmold material encapsulating the wires, one or more portions of the first surface of the first substrate adjacent the conductive elements, and one or more portions of the front surface of second substrate adjacent the plurality of contact pads;
a lens module mounted to the overmold material and not mounted to the third substrate, wherein the lens module comprises a housing and one or more lenses positioned to focus light through the first opening and onto the one or more detectors.

2. The packaged sensor assembly of claim 1, wherein the first substrate is made of a conductive silicon material, and wherein the assembly further comprises an insulation material disposed between the conductive elements and the first substrate.

3. The packaged sensor assembly of claim 1, wherein the one or more detectors include a plurality of photo detectors.

4. The packaged sensor assembly of claim 3, wherein the first opening is disposed over the plurality of photo detectors.

5. The packaged sensor assembly of claim 1, wherein the one or more detectors includes one or more chemical sensors.

6. The packaged sensor assembly of claim 5, further comprising:
a second opening extending from the cavity through the third substrate.

7. The packaged sensor assembly of claim 6, further comprising:
one or more dam structures in the cavity that define a non-linear flow path between the first opening and the second opening.

8. A method of forming a packaged sensor assembly, comprising:
providing a first substrate having opposing first and second surfaces;
forming a plurality of conductive elements each extending between the first and second surfaces;
providing a second substrate that comprises:
opposing front and back surfaces,
one or more detectors formed on or in the front surface, and
a plurality of contact pads formed at the front surface which are electrically coupled to the one or more detectors;
forming a first opening through a third substrate;
forming spacer material directly on the third substrate;
mounting the third substrate to the front surface with an epoxy bonding agent disposed directly between the spacer material and the front surface to define a cavity between the third substrate and the front surface, wherein the first opening extends from the cavity through the third substrate;
placing protective tape on the third substrate and over the first opening;
mounting the back surface to the first surface;
providing a plurality of wires each extending between and electrically connecting one of the contact pads and one of the conductive elements; and
removing the protective tape after the mounting of the back surface to the first surface and after the providing of the plurality of wires.

9. The method of claim 8, further comprising:
encapsulating the wires, one or more portions of the first surface of the first substrate adjacent the conductive elements, and one or more portions of the front surface of second substrate adjacent the plurality of contact pads with an overmold material.

10. The method of claim 9, further comprising:
mounting a lens module to the overmold material and not to the third substrate, wherein the lens module comprising a housing and one or more lenses positioned to focus light through the first opening and onto the one or more detectors.

11. The method of claim 8, wherein the first substrate is made of a conductive silicon material, the method further comprising:
forming an insulation material disposed between the conductive elements and the first substrate.

12. The method of claim 8, wherein the one or more detectors include a plurality of photo detectors.

13. The method of claim 12, wherein the first opening is disposed over the plurality of photo detectors.

14. The method of claim 8, wherein the one or more detectors includes one or more chemical sensors.

15. The method of claim 14, further comprising:
forming a second opening extending from the cavity through the third substrate.

16. The method of claim 15, further comprising:
forming one or more dam structures in the cavity that define a non-linear flow path between the first opening and the second opening.

* * * * *